US012714855B2

(12) United States Patent
Eder et al.

(10) Patent No.: US 12,714,855 B2
(45) Date of Patent: Aug. 25, 2026

(54) CAPACITOR TESTING FOR IMPLANTABLE STIMULATORS

(71) Applicant: Cochlear Limited, Macquarie University (AU)

(72) Inventors: Helmut Christian Eder, Bemboka (AU); Mathew Ross Markey, Macquarie University (AU); Yves Wernaers, Macquarie University (AU); Nick Calus, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 647 days.

(21) Appl. No.: 17/636,983

(22) PCT Filed: Aug. 20, 2020

(86) PCT No.: PCT/IB2020/000700

§ 371 (c)(1),
(2) Date: Feb. 21, 2022

(87) PCT Pub. No.: WO2021/038297

PCT Pub. Date: Mar. 4, 2021

(65) Prior Publication Data

US 2022/0355108 A1 Nov. 10, 2022

Related U.S. Application Data

(60) Provisional application No. 62/892,054, filed on Aug. 27, 2019.

(51) Int. Cl.

| | |
|---|---|
| ***A61N 1/36*** | (2006.01) |
| ***A61N 1/05*** | (2006.01) |
| ***A61N 1/378*** | (2006.01) |

(52) U.S. Cl.
CPC ....... *A61N 1/36038* (2017.08); *A61N 1/0541* (2013.01); *A61N 1/36139* (2013.01); *A61N 1/3787* (2013.01)

(58) Field of Classification Search
CPC .............. A61N 1/36038; A61N 1/0541; A61N 1/36139; A61N 1/3787; A61N 1/36; A61N 1/36046; G01R 31/016; G01R 27/00; G01R 27/2605; G01R 27/2623
See application file for complete search history.

(56) References Cited

U.S. PATENT DOCUMENTS 7,848,804 B1 * 12/2010 Kroll .................... A61N 1/3937 607/2
8,788,032 B2 7/2014 Tsampazis et al.
(Continued)

FOREIGN PATENT DOCUMENTS

WO 02-18962 A1 3/2002

OTHER PUBLICATIONS

"The RC Circuit & Time Constant, Lab Report 007," Professor Todd R. Gelbord, Report Written By Galib F. Rahman, PHYS 1442 Section D783; Nov. 10, 2017; https://openlab.citytech.cuny.edu/grahman-eportfolio/files/2017/12/The-RC-Circuit-Time-Constant.pdf, accessed Jun. 6, 2024. (Year: 2017).*
(Continued)

*Primary Examiner* — Jennifer Pitrak McDonald
*Assistant Examiner* — Christopher J Mutchler
(74) *Attorney, Agent, or Firm* — Edell, Shapiro & Finnan, LLC

(57) ABSTRACT

Examples disclosed herein are relevant to testing capacitors to identify potentially faulty DC blocking capacitors in implantable stimulators. In an example, the test includes selecting an active electrode, a return electrode, and a reference electrode. Short duration monophasic stimulation is used to charge up the DC blocking capacitors of the active and return electrodes. The electrodes are subsequently dis-
(Continued)

connected from all other nodes except a discharge circuit (e.g., a star circuit) and the tissue. The reference electrode is used to measure the voltage of the DC blocking capacitor of the active electrode during the charging phase and the discharging phase (via the discharge circuit). The characteristics of one or more of the capacitors charging or discharging can be sensed and then analyzed to determine whether the one or more capacitors are functioning properly. Faulty capacitors can be identified by comparing actual and expected characteristics.

20 Claims, 9 Drawing Sheets

(56) References Cited

U.S. PATENT DOCUMENTS 9,409,017 B2 8/2016 Tsampazis et al.
9,700,724 B2 7/2017 Liu et al.
9,717,906 B2 8/2017 Karunasiri
9,853,655 B1 * 12/2017 Pernull ............... H03M 1/1071
2003/0187485 A1 10/2003 Sturman et al.
2004/0225327 A1 11/2004 Norton et al.
2011/0077698 A1 3/2011 Tsampazis et al.
2014/0114592 A1 * 4/2014 Eilertsen ................ G01R 31/64
702/58
2018/0140831 A1 5/2018 Feldman et al.
2019/0175904 A1 * 6/2019 Baru .................... A61N 1/0551

OTHER PUBLICATIONS

X. Liu et al., "A Stimulator Output Stage with Capacitor Reduction and Failure-Checking Techniques," 2006 IEEE International Symposium on Circuits and Systems (ISCAS), Island of Kos, 2006, pp. 641 pp. -644. (Year: 2006).*

International Search Report and Written Opinion in counterpart International Application No. PCT/IB2020/000700, mailed Dec. 14, 2020, 10 pages.

* cited by examiner

CAPACITOR TESTING FOR IMPLANTABLE STIMULATORS

This application is being filed on Aug. 20, 2020, as a PCT International Patent application and claims priority to U.S. Provisional patent application Ser. No. 62/892,054, filed Aug. 27, 2019, the entire disclosure of which is incorporated by reference in its entirety.

BACKGROUND

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In an example, there is a method that includes: selecting one or more electrodes of a plurality of electrodes of an implantable stimulator for an active electrode set; selecting one or more electrodes of the plurality of electrodes for a return electrode set; charging one or more active electrode capacitors associated with the active electrode set; charging one or more return electrode capacitors associated with the return electrode; disconnecting the return electrode set, the active electrode set, the one or more active electrode capacitors, and the one or more return electrode capacitors; after disconnecting, measuring one or more characteristics of the one or more active electrode capacitors during discharge of the one or more active electrode capacitors; and determining a health of one or more of the one or more active electrode capacitors based on the one or more characteristics.

In another example, there is an apparatus that includes a stimulation source; a plurality of electrode subcircuits, a discharge circuit connected to each of the plurality of electrode subcircuits; and one or more processors. Each respective electrode subcircuit includes a capacitor an electrode connected in series to the capacitor and being configured to deliver stimulation to tissue using the stimulation source; and a switch connected to the capacitor and configured to selectively couple the capacitor with the stimulation source. The one or more processors are configured to test a health status of a respective capacitor of a respective subcircuit of the electrode subcircuits via a test that includes determining discharge characteristics of the respective capacitor while discharging via the discharge circuit.

In yet another example, there is a method that includes charging a first capacitor and a second capacitor; after charging the first capacitor and the second capacitor, electrically disconnecting the first capacitor and the second capacitor from all nodes except for tissue and a discharge circuit; allowing the first capacitor to discharge via the discharge circuit; measuring charge or discharge characteristics of the first capacitor; and determining a health status of the first capacitor based on the charge or discharge characteristics.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
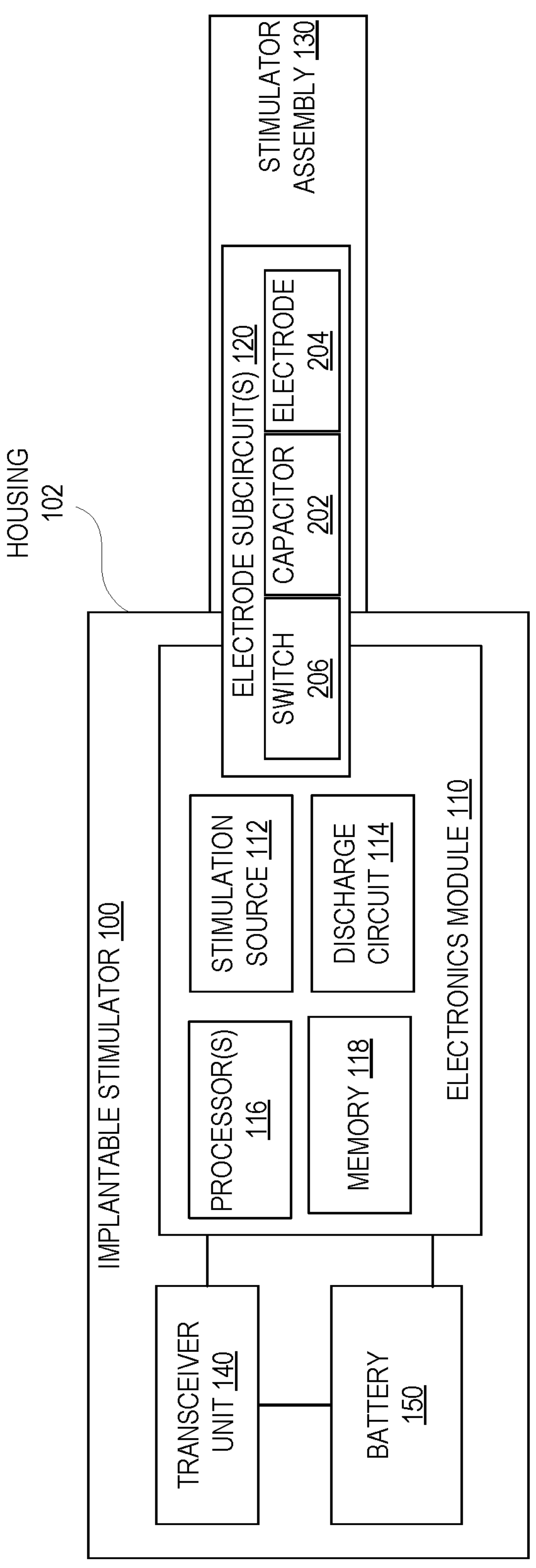
FIG. 1 illustrates an example functional diagram of an implantable stimulator that can benefit from technology herein.

Disclosed technology relates to testing capacitors, particularly capacitors used in medical devices. For medical devices that provide stimulation to target tissue (e.g., cochlear implants, cardiac stimulators, and neurostimulators, among others), electrodes can contact the target tissue and be used to provide stimulation. Each of such electrodes can be connected to a capacitor to limit the flow of DC (Direct Current) energy into the tissue. Passing DC energy through a capacitor builds up charge in the capacitor and increases voltage of the capacitor. Eventually, the amount of voltage is high enough that further charge flow through the capacitor is prevented. In this manner, capacitors can act as a safety mechanism to limit the flow of DC energy into the tissue in an unbalanced manner. Passing DC energy into tissue in an unbalanced manner can be undesirable because the energy can potentially damage tissue and cause undesirable buildup proximate the electrode, which can ultimately require removal of the stimulator.

To avoid undesirable side effects of passing DC energy into tissue, stimulator devices can provide charge-balanced stimulation whereby zero net charge is passed into the tissue. For example, a cochlear implant that electrically stimulates nerves inside the cochlea in order to produce the sensation of sound for a recipient can be configured to provide stimulation in biphasic pulses. These pulses can provide energy quickly in one direction and then in the opposite direction so the overall net effect is that substantially no DC energy has been delivered to the tissue.

However due to varying factors of circuit accuracies, timing deviations, or other effects, the DC flow can possibly be unbalanced under some rare circumstance. For this reason, some stimulators include a capacitor in series with each electrode connected to tissue. These capacitors can be referred to as DC blocking capacitor. DC flow through a DC blocking capacitor would result in the capacitor charging and eventually reaching a maximum voltage, thereafter blocking any further current flowing into the tissue until the voltage decreases. Under normal operating conditions, the capacitors simply charge and discharge with every pulse of the biphasic stimulus. The first phase charges up the capacitor, and the second phase discharges the capacitor. Any residual charge that may remain on the capacitors is discharged during the inter-stimulus gap, during which time all electrodes can be shorted to the tissue potential by the stimulator.

But, over time, a capacitor can develop a fault. For example, a capacitor can develop a leak or dendritic growth (e.g., from one side of the capacitor to another side) can occur. These or other failure modes can prevent the capacitors from holding charge. Once a capacitor fails to hold a charge, the capacitor also fails to offer the same protection against net DC flow into the tissue. This failure is difficult to detect. During normal use, a failed capacitor may have little to no discernable effect on the operation of the stimulator. The stimulator would behave similarly to one having a normally-functioning capacitor until the capacitor fails to block DC flow. But even then, such a failure can be difficult to detect in the short term.

Disclosed technology is relevant to detecting failed or failing capacitors. The technology can be used to identify failing capacitors prior to any need for them to block DC. The tests can be executed at regular intervals to check that the DC blocking capacitors are capable of performing their intended operation if and when required. The tests can be performed after implantation of the medical device in which the capacitors are used.

In examples, prior to performing the test, certain capacitors can be excluded. For example, any capacitors associated with non-functioning electrodes (e.g., open circuit electrodes or shorted electrodes) or capacitors having an abnormal impedance range can be excluded from selection as part of the test. In addition, prior to performance of the test, the implantable stimulator can be disabled from providing therapeutic stimulation during the test.

In an example, the test includes selecting an active electrode, a return electrode, and a reference electrode. Short duration monophasic stimulation is used to charge the DC blocking capacitors of the active and return electrodes. The electrodes are subsequently disconnected from all other nodes except a discharge circuit (e.g., a star circuit) and the tissue. The reference electrode is used to measure the voltage of the DC blocking capacitor of the active electrode during the charging phase and the discharging phase (via the discharge circuit). The characteristics of one or more of the capacitors charging or discharging can be sensed and then analyzed to determine whether the one or more capacitors are functioning properly. The characteristics can include, for example, the rate of charge and discharge of the capacitor. The expected charge and discharge rates of a properly-functioning capacitor is able to be determined in advance (e.g., can be predetermined or calculated using predetermined values). So faulty capacitors can be identified by comparing the rate of charge or discharge of the capacitor with the expected value. In many examples, the faulty capacitor would not hold a charge for as long as healthy capacitors, if it can hold a charge at all.

If a faulty capacitor is identified, then remediation can be performed. The particular remedies can vary depending on the type of stimulator. In many examples, an alert can be provided to the recipient of the stimulator as well as a caregiver or clinician. In some examples (e.g., where the stimulator is a cochlear implant), an electrode associated with the faulty capacitor can be disabled (e.g., removed from use as part of normal stimulation) and the stimulation can be remapped to limit the effect of the disabled electrode on the ability of the stimulator to properly provide stimulation. For some kinds of stimulators (e.g., cardiac pacing stimulators or neurostimulators), a balance of considerations may weigh in favor of not disabling the electrode, but sending an alert to relevant clinicians to have the issue addressed under clinical supervision. For instance, the relative negative effect of an electrode failing to have a functioning DC-blocking capacitor may be outweighed by the benefit of having a properly functioning electrode.

The tests can be performed in any of a variety of circumstances. For instance, the tests can be performed as part of a routine fitting or check-in by a clinician. For example, the clinician may have a programmer or other device that connects with the stimulator and causes the test to be performed. The programmer can run fitting software that calls certain functions inside the implant to perform the test. In addition or instead, the test may be performed automatically by the stimulator. For instance, the test may be performed on start-up of the stimulator.

Figure 7:
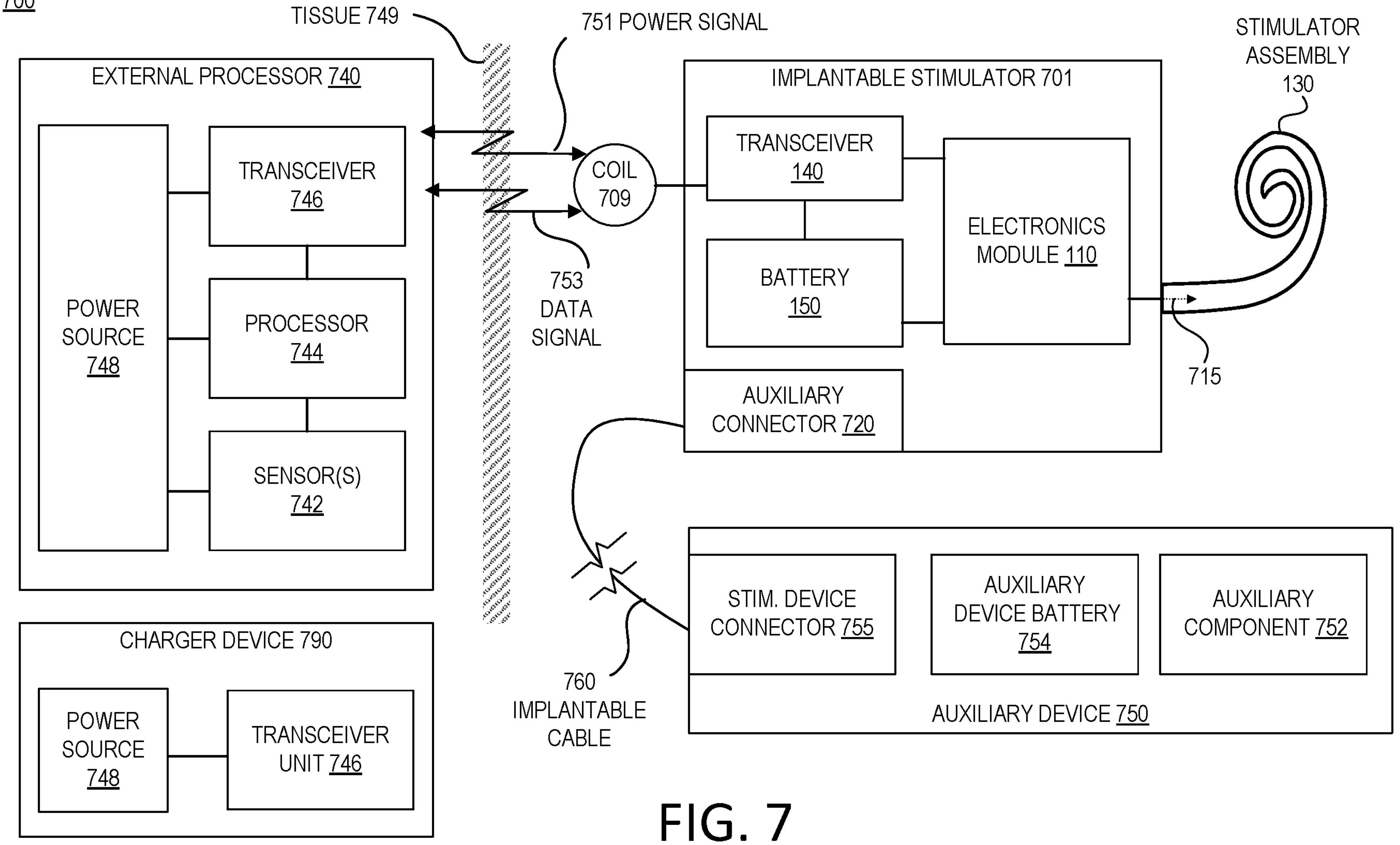
FIG. 7 is a functional block diagram of an implantable stimulator system that can benefit from techniques described herein.

Technology described herein can be applied to any of a variety of medical devices, particularly implantable stimulators. Example stimulator devices that can benefit from technology herein are shown in FIG. 1 and FIG. 7. As a specific example, technology herein can be used with a cochlear implant, an example of which is described herein in conjunction with FIG. 8. Additional example cochlear implants are described in, for instance, U.S. Pat. Nos. 4,532,930; 6,537,200; 6,565,503; 6,575,894; and 6,697,674, which are hereby incorporated by reference herein for any and all purposes. As another specific example, the technology disclosed herein can be applied to visual prostheses, such as the visual prosthesis described in conjunction with FIG. 9. Additional medical devices that can benefit from technology herein include neurostimulators, cardiac pacemakers, cardiac defibrillators, sleep apnea management stimulators, seizure therapy stimulators, tinnitus management stimulators, and vestibular stimulation devices, as well as other medical devices that deliver stimulation to tissue. An example implantable stimulator that can benefit from technology herein is described in FIG. 1.

Example Implantable Stimulator

FIG. 1 is a functional diagram of an implantable stimulator 100 that can benefit from technology herein. The implantable stimulator 100 can take any of a variety of different forms, such as a cochlear implant, a neurostimulator, a vestibular stimulation device, a tinnitus management stimulator, or a visual prosthesis, among other kinds of implantable stimulators. The implantable stimulator 100 can be configured as a totally-implantable device such that the implantable stimulator can provide stimulation without the need for receiving data from an external device. In such a totally-implantable configuration, the implantable stimulator 100 may nonetheless be configured to be charged from an external device and even receive data from the external device.

The implantable stimulator 100 can have one or more components disposed within a biocompatible housing 102, as well as one or more components extending from or entirely outside of the biocompatible housing 102. As illustrated, the implantable stimulator 100 includes an electronics module 110, one or more electrode subcircuits 120, a stimulator assembly 130, a transceiver unit 140, and a battery 150, among other components.

The electronics module 110 is a module of one or more other components that provide stimulator device functionality. In many examples, the electronics module 110 includes one or more components for receiving a signal and generating and controlling delivery of a stimulation signal via the stimulator assembly based on the signal. The electronics module 110 can generate or control delivery of the stimulation signals to the stimulator assembly 130. As illustrated, the electronics module 110 can further include a stimulation source 112, a discharge circuit 114, one or more processors 116, and memory 118.

The stimulation source 112 is a component that generates electrical stimulation signals for use in stimulating target tissue. The stimulation source 112 can use or generate stimulation control signals to generate electrical stimulation signals for delivery to target tissue via one or more of the electrode subcircuits 120. The stimulation can be monopolar or multi-polar electrical stimulation. In many examples, the stimulation source 112 includes a current source/sink that produces current pulses based on input received from a decoder. The stimulation source 112 can further include a voltage source.

Figure 2:
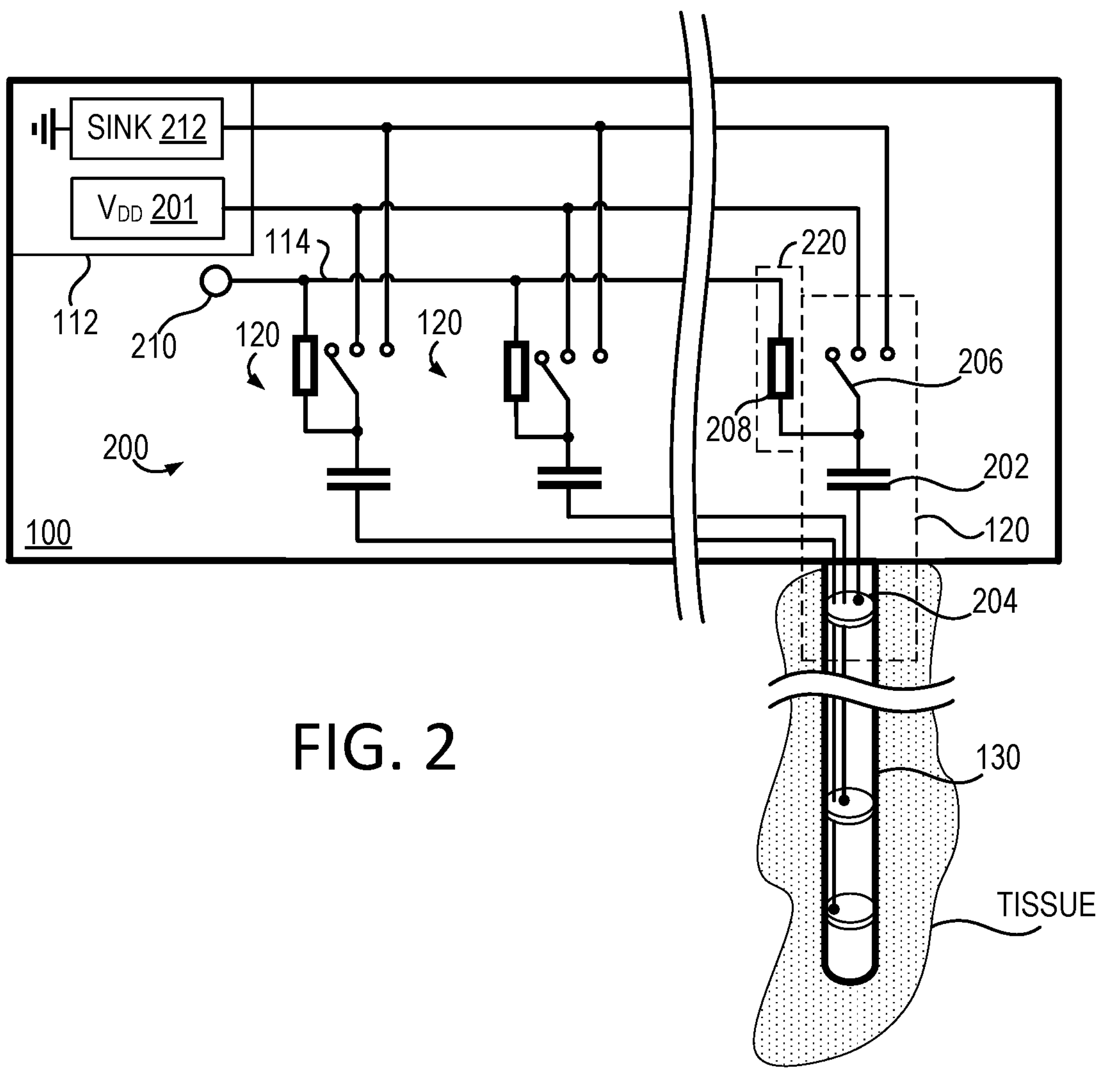
FIG. 2 illustrates a simplified view of subcircuits of the implantable stimulator in an example configuration that can benefit from technology disclosed herein.

The discharge circuit 114 is a circuit configured to passively dissipate charge from the one or more electrode subcircuits 120. In particular, the discharge circuit 114 can be configured to discharge a charge built up on electrodes and capacitors of the one or more electrode subcircuits. The discharge circuit 114 can dissipate buildup that occurs due to, for example, disconnect or shutdown of one or more components associated with the implantable stimulator 100. For instance, where the implantable stimulator 100 is a cochlear implant having an external component, if the recipient of the cochlear implant removes the external device during stimulation by the implantable stimulator 100, then there can be charge remaining on the electrode. The discharge circuit 114 can beneficially allow dissipation of such charge. The discharge circuit 114 can further be used to discharge charge built up on capacitors of the electrode sub circuits 120 as part of a test of capacitor health. The discharge circuit 114 can be configured in any of a variety of ways. In an example, the discharge circuit 114 includes a star node connected to each of the plurality of electrode subcircuits via a discharge subcircuit that includes a resistor having a sufficiently high resistance as to not disrupt therapeutic stimulation by the electrode subcircuits. A specific example configuration of the discharge circuit 114 is shown in FIG. 2.

The one or more processors 116 are one or more electronic components that perform stimulation-related functions to control one or more components of the implantable stimulator 100. For instance, the one or more processors 116 can open or close switches to control the flow of stimulation to electrodes. The one or more processors 116 include one or more microprocessors configured to receive input and produce output based thereon (e.g., typically controlling one or more aspects or operations of the implantable stimulator 100). The one or more processors 116 can include one or more application-specific integrated circuits or field programmable gate arrays. In addition to or instead, the one or more processors 116 can be one or more processors (e.g., central processing units) that execute instructions (e.g., as stored in the computer-readable medium 118) to produce results.

The memory 118 can be one or more software- or hardware-based processor-readable (e.g., computer-readable) storage media operable to store information (e.g., data or instructions) accessible by the one or more processors 116. The memory 118 can store, among other things, instructions executable by the one or more processors 116 to cause performance of operations described herein, as well as other data. The memory 118 can be volatile memory (e.g., RAM), non-volatile memory (e.g., ROM), or combinations thereof. The memory 804 can include transitory memory or non-transitory memory. The memory 804 can also include one or more removable or non-removable storage devices. In examples, the memory 804 can include RAM, ROM, EEPROM (Electronically-Erasable Programmable Read-Only Memory), flash memory, optical disc storage, magnetic storage, solid state storage, or any other memory media usable to store information for later access. In examples, the memory 804 encompasses a modulated data signal (e.g., a signal that has one or more of its characteristics set or changed in such a manner as to encode information in the signal), such as a carrier wave or other transport mechanism and includes any information delivery media.

The one or more electrode subcircuits 120 are each subcircuits that include an electrode (e.g., electrode 204 of FIG. 2) for providing stimulation to target tissue. The electrode subcircuits 120 can be ultimately connected to the electronics module 110 (e.g., to the stimulation source 112 thereof) and produce output based signals received therefrom. In an example implementation, each electrode subcircuit 120 includes a capacitor (e.g., capacitor 202 of FIG. 2) connected to the electrode in series for limiting DC flow to the target tissue. Each electrode subcircuit 120 can further include a switch (e.g., switch 206 of FIG. 2) for controlling the flow of stimulation to or from the electrode. As illustrated, the electrode subcircuits 120 need not be entirely disposed within or outside of the biocompatible housing 102.

The stimulator assembly 130 includes the one or more components of the implantable stimulator that deliver stimulation signals to target tissue. In many examples, the stimulator assembly includes an elongate lead on or in which an array of electrodes is disposed. The lead can be configured to place and hold the electrodes into contact with a desired location proximate target tissue. Where the implantable stimulator 100 is a cochlear implant, the stimulator assembly 130 can take the form of (or have one or more characteristics or components of) the carrier members described in U.S. Pat. No. 8,249,724, which is titled "Elongate implantable carrier member having an embedded stiffener" and which is hereby incorporated by reference herein in its entirety for any and all purposes.

The transceiver unit 140 is a component configured to transmit and/or receive signals to/from another component.

For example, the transceiver unit 140 can be configured to transcutaneously receive a power signal and/or a data signal from the external processor device. The transceiver unit 140 can be a collection of one or more implanted components that form part of a transcutaneous energy or data transfer system. Further, transceiver unit 140 can include any number of components that receive or transmit a power signal or data signal, such as a coil for a magnetic inductive arrangement, an antenna for an alternative RF system, capacitive plates, or any other suitable arrangement. Various types of energy transfer, such as electromagnetic, capacitive and inductive transfer, can be used to usably receive the power signal and/or the data signal from the external processor device at the implantable stimulator 100.

The battery 150 is a component configured to store power and provide power to the other components of the implantable stimulator 100 as needed for operation. The battery 150 can include, for example, one or more rechargeable batteries. Power can be received from an external device, such as an external processor device or external charger device, and stored in the battery 150. In other examples, the implantable stimulator 100 can include an energy scavenging component to charge the battery 150.

Example Circuit

FIG. 2 illustrates a simplified view of subcircuits 200 of the implantable stimulator 100 in an example configuration that can benefit from techniques disclosed herein. The illustrated subcircuits 200 include the discharge circuit 114, the electrode subcircuits 120, a voltage source 201, and a current sink 212.

In the illustrated example, the discharge circuit 114 is configured as a star circuit having a star node 210 connected to each of the plurality of electrode subcircuits 120 via a respective discharge subcircuit 220. The discharge subcircuit 220 can include one or more components, including a resistor 208. The resistor 208 can have a sufficiently high resistance to not disrupt therapeutic stimulation provided by the electrode subcircuits 120. In an example, the resistor 208 has a resistance of at least 100 kilo-ohms. In another example, the resistor 208 has a resistance of at least 5 megaohms. In another example, the resistor 208 can have a resistance selected to be greater than a resistance limit of a capacitor 202 that is faulty.

Each respective electrode subcircuit 120 is a subcircuit of the implantable stimulator 100 that includes at least an electrode 204 configured to stimulate tissue. In the illustrated example, each electrode subcircuit 120 further includes a capacitor 202 connected in series with the electrode 204. Also illustrated is a switch 206 connected to the capacitor 202. The capacitor 202 can be a DC limiting capacitor configured to limit the flow of DC to the target tissue via a connected electrode 204. The electrode 204 can be a component configured to deliver stimulation to tissue. The switch 206 can be a component configured to selectively couple the capacitor 202 and/or the electrode 204 with the voltage source 201. The switches 206 of the electrode subcircuits 120 can be controlled by a switch controller of the implantable stimulator 100. The illustrated example further includes electrode subcircuits 120 having a switch 206 to selectively couple the capacitor 202 and/or the electrode to the current sink 212.

In an example implementation, the illustrated subcircuits 200 can cause bipolar stimulation in the following manner. Under control of a decoder (not shown), the current sink 212 produces a current pulse. To generate the first phase of the output pulse, a first switch 206 is set to connect a first electrode 204 to the voltage source 201 and a second switch 206 is set to connect a second electrode to the current sink 212. All other switches 206 are disconnected (e.g., set to open circuit). The current pulse from the current sink 212 is thereby directed between the first and second electrodes 204 selected by switches 206. An inter-phase gap (e.g., a brief pause between the first and second pulses which make up the biphasic stimulation waveform) is generated by briefly setting all of the switches 206 to the open position. To generate the second phase, the second switch 206 is thrown to connect the second electrode 204 to the voltage source 201. At the same time the first switch 206 is thrown to connect the first electrode 204 to the current sink 212. The current sink 212 then generates a second pulse (e.g., having equal amplitude and duration to the first pulse), which is applied through the two selected electrodes 204 in the reverse direction to the first pulse. This process produces a biphasic pulse between the first and second electrodes 204 to stimulate target tissue. The two phases of the current pulse are both produced by the same current sink 212 and so are closely matched. This close matching can result in relatively low amounts of residual charge on the electrodes 204. Once the two phases of the pulse have been delivered, any residual charge remaining on the electrodes 204 can be allowed to discharge.

This process can be modified to provide monophasic stimulation by providing the first phase of the output pulse but not the second phase of the output pulse. The process can also be modified to provide monopolar stimulation when one of the two selected electrodes is an electrode external to the treatment area (e.g., an extracochlear electrode). A common ground pulse can be produced by connecting all but one switch 206 first to the voltage source 201, with the exceptional switch 206 being connected to the current sink 212. The switch 206 positions are then reversed to deliver the second phase of the biphasic pulse.

First Example Process

Figure 3:
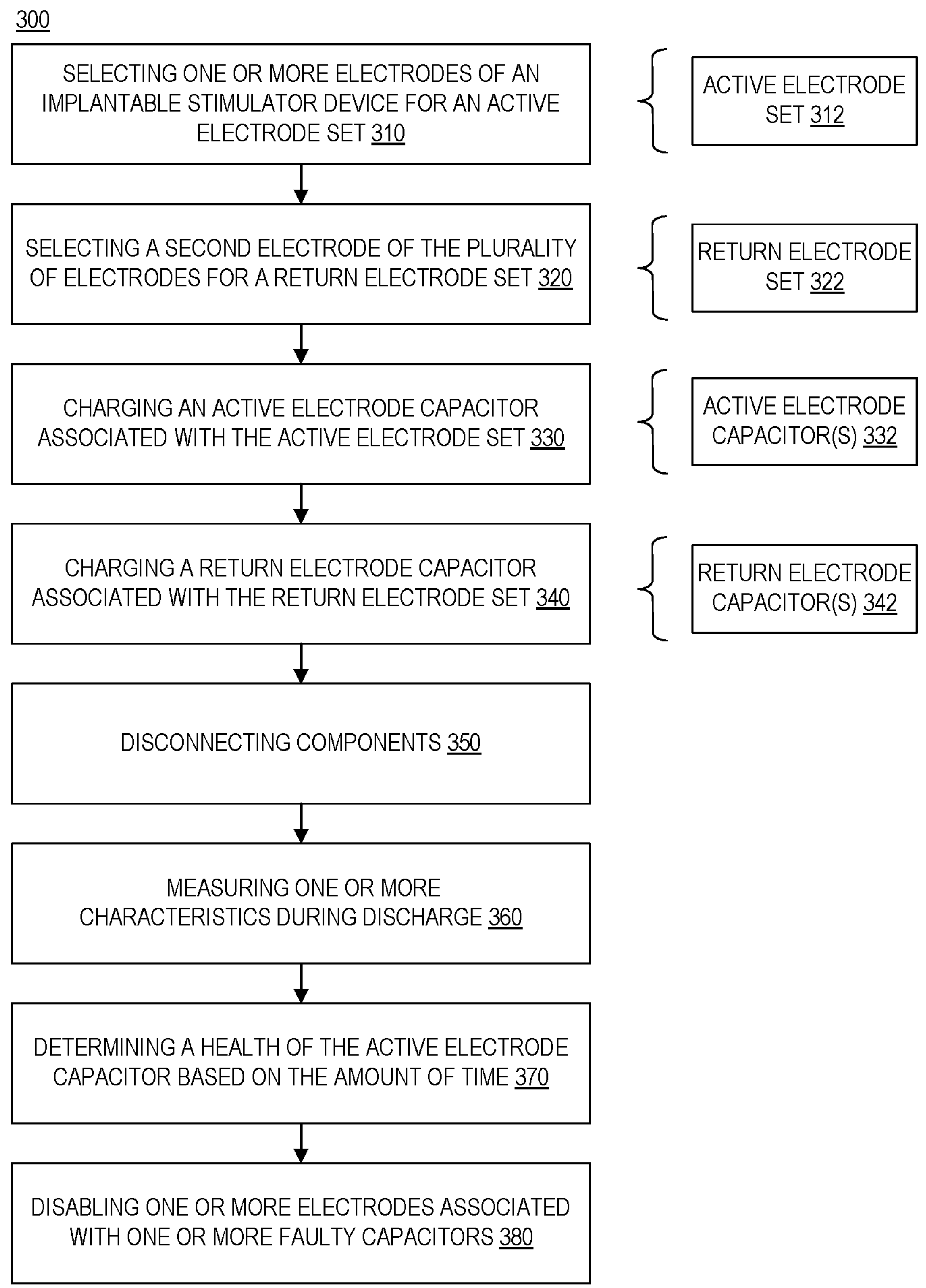
FIG. 3 illustrates a first example process for testing capacitors of an implantable stimulator in accordance with certain examples herein.

FIG. 3 illustrates a first example process 300 for testing one or more capacitors 202 of an implantable stimulator 100. The process 300 can be performed at any of a variety of times or situations. In an example, the process 300 is performed as part of a power-on process of the implantable stimulator 100. For instance, some or all of the capacitors can be tested whenever the implantable stimulator 100 is powered on or activated from a sleep mode or reduced-power state. An implantable stimulator 100 having ten electrodes can test two electrodes each time the device is powered on such that over time all electrodes are tested. This can allow for regular testing of capacitor health without substantially delaying a power-on process to do so. In another example, the process 300 is be performed during a fitting of the implantable stimulator 100 or during a maintenance operation on the implantable stimulator 100. In some examples, the process 300 can be performed responsive to receiving a function call from a device. The device can be a mobile consumer device (e.g., a phone or tablet), a fitting device, a maintenance device, or another device. The function call can cause execution of a script describing operations to perform, including those described herein in relation to process 300. The script can be stored, for example, in the memory 118.

The process 300 can begin with operation 310. Operation 310 includes selecting 310 one or more electrodes 204 of a plurality of electrodes 204 of the implantable stimulator 100 for an active electrode set 312. The active electrode set 312 is a set of one or more electrodes that will be used as active electrodes during the testing process 300. Following operation 310, the flow of the process 300 can move to operation 320, which includes selecting one or more electrodes 204 of the plurality of electrodes 204 of the implantable stimulator 100 for a return electrode set 322. The return electrode set 322 is a set of one or more electrodes that will be used as return electrodes during the testing process 300.

The selection of the electrodes 204 can be performed in any of a variety of manners. In many examples, the process 300 is performed as part of a larger assessment plan. For instance, the process 300 can be repeated for multiple pairs of electrodes 204 of the implantable stimulator 100. The process 300 can be repeated for each pair of electrodes 204 or each pair of DC blocking capacitors 202 of the implantable stimulator 100. In some examples, the sets of electrodes to be tested are described in an assessment plan. The assessment plan can specify a plurality of assessments and, for each assessment, the plan can specify which one or more electrodes are to be selected as part of the active electrode set 312 and the return electrode set. The assessment plan typically requires the performance of several assessments until all of the relevant capacitors have been assessed. In an example assessment plan, the plan includes assessments based on pairs of electrodes 204 and specifies which one or more electrodes 204 are to be selected as part of the active electrode set 312 and the return electrode set 322. (e.g., a first electrode 204 of the pair is selected as part of the active electrode set 312 and a second electrode 204 of the pair is selected as part of the return electrode set 322). For instance, the assessment plan can include a first assessment of a first electrode 204 (and associated one or more capacitors 202) and a second electrode (and associated one until each assessing several subsets of all of the capacitors 202). The first assessment can specify that the active electrode set 312 is to include only the first electrode and the return electrode set 322 is to include only the second electrode. An example assessment plan having n assessments for an implant having n electrodes is shown below:

TABLE I

| Assessment Plan | | | | | | | | | |
|---|---|---|---|---|---|---|---|---|---|
| Assessment No. | 1 | 2 | 3 | 4 | 5 | 6 | . . . | n − 1 | n |
| Active Set Electrode Nos. | {1} | {2} | {3} | {4} | {5} | {6} | . . . | {n − 1} | {n} |
| Return Set Electrode Nos. | {2} | {3} | {4} | {5} | {6} | {7} | . . . | {n} | {1} |

Using the assessment plan a next active electrode set and active return set can be selected. For example, if a next assessment is assessment 2, then electrodes 2 and 3 can be selected for the active electrode set 312 and the return electrode set 322 respectively.

Following the selection of the one the electrodes in operations 310 and 320, the flow of the process 300 can move to operation 330.

Operation 330 includes charging the one or more active electrode capacitors 332 associated with the active electrode set 312. Operation 340 includes charging one or more return electrode capacitors 342 associated with the return electrode set 322. The capacitors 332, 342 can be charge by providing monophasic stimulation to the capacitors 332, 342. Following the charging of the active electrode capacitors 332 and the return electrode capacitors 342 in operations 330 and 340, respectively, the flow of the process 300 can move to operation 350.

Operation 350 includes disconnecting components. This operation 350 can include disconnecting the electrodes 204 of the return electrode set 322, the electrodes of the active electrode set 312, the one or more active electrode capacitors 332, and the one or more return electrode capacitors 342. The disconnecting can include disconnecting the components form a stimulation source 112. The disconnecting can be performed via the respective switches 206 of the electrode subcircuits 120. In an example, the disconnecting can include disconnecting one or more capacitors 202 and electrodes 204 from the voltage source 201 and the current sink 212.

After being disconnected, the components can be allowed to discharge, such as over the discharge circuit 114, which can include a star circuit of resistors 208. Following operation 350, the flow of the process 300 can move to operation 360.

Operation 360 includes measuring one or more characteristics of the one or more active electrode capacitors 332 during discharge of the one or more active electrode capacitors. In an example, the one or more characteristics include an amount of time taken to discharge the one or more of the active electrode capacitors 332. In another example, the one or more characteristics include a discharge curve of the one or more active electrode capacitors 332. Measuring the characteristics can be performed by, for example, measuring an amount of voltage stored by the one or more active electrode capacitors 332 over time. The voltage can be measured using, for instance, voltage telemetry. A reference electrode can be selected and used to measure the voltage. Following operation 360, the flow of the process can move to operation 370.

Operation 370 includes determining a health of one or more of the one or more active electrode capacitors 332 based on the one or more characteristics. Where the one or more characteristics include an amount of time taken to discharge a capacitor, determining the health can include determining that one or more of the one or more active electrode capacitors 332 is faulty responsive to the amount of time taken to discharge the capacitor failing to satisfy a predetermined threshold. For example, the predetermined threshold can be set to a discharge time of a known healthy capacitor or a calculated health capacitor discharge time calculated based on known characteristics of components of the implantable stimulator (e.g., based on the capacitance of the capacitors, the resistance of the resistors, etc.). Likewise, a charge time can be determined and compared to a threshold. Where the one or more characteristics include a charge or discharge curve, the resulting charge or discharge curve for the one or more active electrode capacitors 332 can be determined and analyzed to detect whether the one or more active electrode capacitors 332 are healthy or faulty. Following operation 370, the flow of the process can move to operation 380 when one or more electrode capacitors 332 are faulty.

Operation 380 includes disabling one or more electrodes 204 associated with one or more faulty capacitors 202. For instance, the method 300 can include (e.g., as part of operation 370, 380, or another operation) identifying one or more faulty capacitors based on the determined health and disabling one or more electrodes associated with the one or more faulty capacitors. In addition to or instead of disabling the one or more electrodes 204, an alert can be provided to the recipient or a clinician to provide information regarding the faulty capacitor 202. In addition to or instead of disabling the one or more electrodes 204 a remediation action can be performed to remediate the one or more faulty capacitors 202.

In some examples, the process 300 can further include stimulating target tissue with the active electrode set 312. For instance, the target tissue can be cochlear tissue.

Second Example Process

Figure 4:
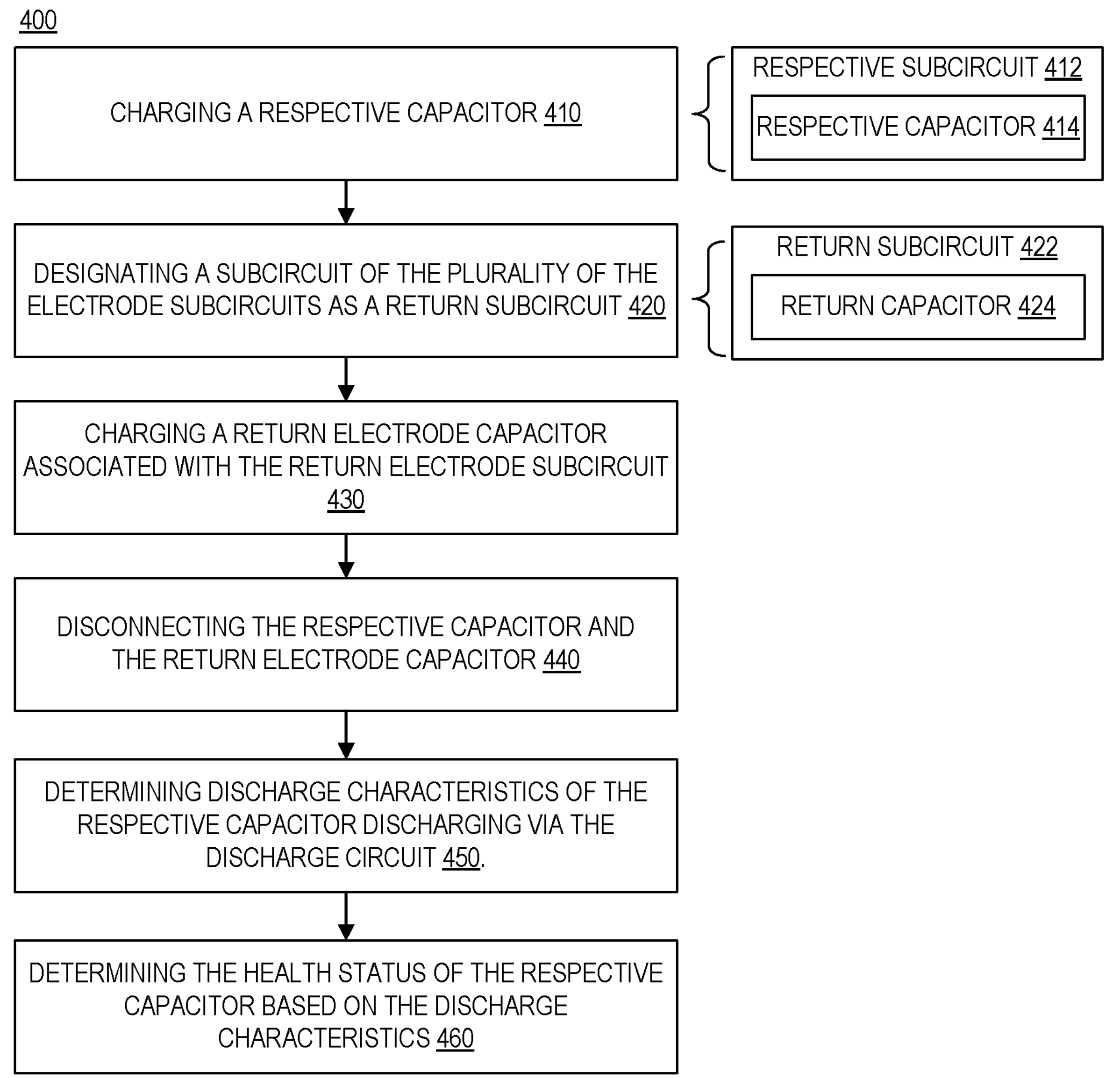
FIG. 4 illustrates a second example process for testing capacitors of an implantable stimulator in accordance with certain examples herein.

FIG. 4 illustrates a second example test process 400 that can be performed. The process 400 can be performed by an apparatus, such as the implantable stimulator 100 responsive to the occurrence of particular events, such as during a power-on process of the implantable stimulator 100, during a fitting of the implantable stimulator 100, or at another time. This process 400 can be performed by an implantable stimulator 100 that includes, among other components, a stimulation source 112, a discharge circuit 114 connected to each of a plurality of electrode subcircuits 120, and one or more processors 116 configured to test a health status of a respective capacitor 414 of a respective subcircuit 412 of the electrode subcircuits 120 via the test process 400. The one or more processors 116 can be so configured by, for example, being connected to a computer-readable medium of the implantable stimulator 100. The computer-readable medium 118 can store instructions that, when executed by the one or more processors 116 cause the one or more processors 116 to perform the test process 400 (e.g., by performing the operations thereof), thereby configuring the one or more processors 116 to test the health of the respective capacitor 414 of a respective subcircuit 412 of the electrode subcircuits 120 via the test 400. Each of the electrode subcircuits 120 can have a capacitor 202, an electrode 204 connected in series to the capacitor and being configured to deliver stimulation to tissue using the stimulation source 112, and a switch 206 connected to the capacitor 202 and configured to selectively couple the capacitor 202 with the stimulation source 112. The stimulation source 112 can be configured to provide biphasic stimulation. In an example, the test process 400 includes an operation 450 that includes determining discharge characteristics of the respective capacitor 414 while discharging via the discharge circuit 114. In some examples, operation 450 is performed in conjunction with other operations. For instance, the process 400 can begin with operation 410.

Operation 410 includes charging the respective capacitor 414 of a respective subcircuit 412. The respective capacitor 414 can be selected according to an assessment plan or in another manner. The respective capacitor 414 can be charged via a monophasic pulse produced by the stimulation source 112. For instance, the process 400 can be configured to charge the respective capacitor 414 for an amount of time that would charge the capacitor 414 to capacity, were the capacitor functioning normally. Following operation 410, the flow of the process 400 can move to operation 420.

Operation 420 includes designating a subcircuit of the plurality of electrode subcircuits as a return subcircuit 422 having a return capacitor 424. The return subcircuit 422 can be designated based on an assessment plan or using another criteria. Following operation 420, the flow of the process 400 can move to operation 430.

Operation 430 includes charging a return electrode capacitor 424 associated with the return subcircuit 422. The return electrode capacitor 424 can be charged via, for example, a monophasic stimulation pulse provided by the stimulation source 112. Following operation 430, the flow of the process can move to operation 440.

Operation 440 includes disconnecting the respective capacitor 414 and the return capacitor 424 of the return subcircuit 422 (e.g., prior to determining the discharge characteristics of the respective capacitor 414 in operation 450 discharging via the discharge circuit 114). This operation 440 can include, for example, disconnecting the respective capacitor 414 and the return capacitor 424 from other paths except for a path to the tissue (e.g., via electrodes 204 of the subcircuits) and a path to the discharge circuit 114. This can include actuating switches 206 of the subcircuits to disconnect the respective capacitor 414 and the return capacitor 424 from the stimulation source 112. Following operation 440, the flow of the process 400 can move to operation 450.

Operation 450 includes determining discharge characteristics of the respective capacitor 414 while the respective capacitor 414 is discharging via the discharge circuit 114. As described above, the discharge circuit 114 can include a node 210 connected to each of the plurality of electrode subcircuits 120 via a respective discharge subcircuit 220 having a resistor 208. The discharge circuit 114 can connect to each respective electrode subcircuit 120 of the plurality of electrode subcircuits 120 at a location between a capacitor 202 and a switch 206 of the respective electrode subcircuit 120. Determining the discharge characteristics can include monitoring the voltage or other parameters of the respective capacitor 414, such as via voltage telemetry. The monitoring can occur over time. Following operation 450, the flow of the process 400 can move to operation 460.

Operation 460 includes determining a health status of the respective capacitor 414 based on the discharge characteristics. As described elsewhere, the discharge characteristics can be compared discharge characteristics that would be expected for healthy capacitors 202. If the difference between the discharge characteristics of the respective capacitor 414 and one or more characteristics expected if the respective capacitor 414 were healthy is greater than a predetermined threshold, then the respective capacitor 414 can be determined to be faulty.

Responsive to the respective capacitor 414 being healthy or unhealthy, any of a variety of actions can be taken. For instance, as described elsewhere herein, responsive to the respective capacitor 414 being faulty, an electrode 204 of the respective subcircuit 412 can be disabled and the recipient can be alerted. The characteristics can be stored (e.g., in the memory 118) for later use and auditing (e.g., to track healthy of capacitors over time).

Third Example Process

Figure 5:
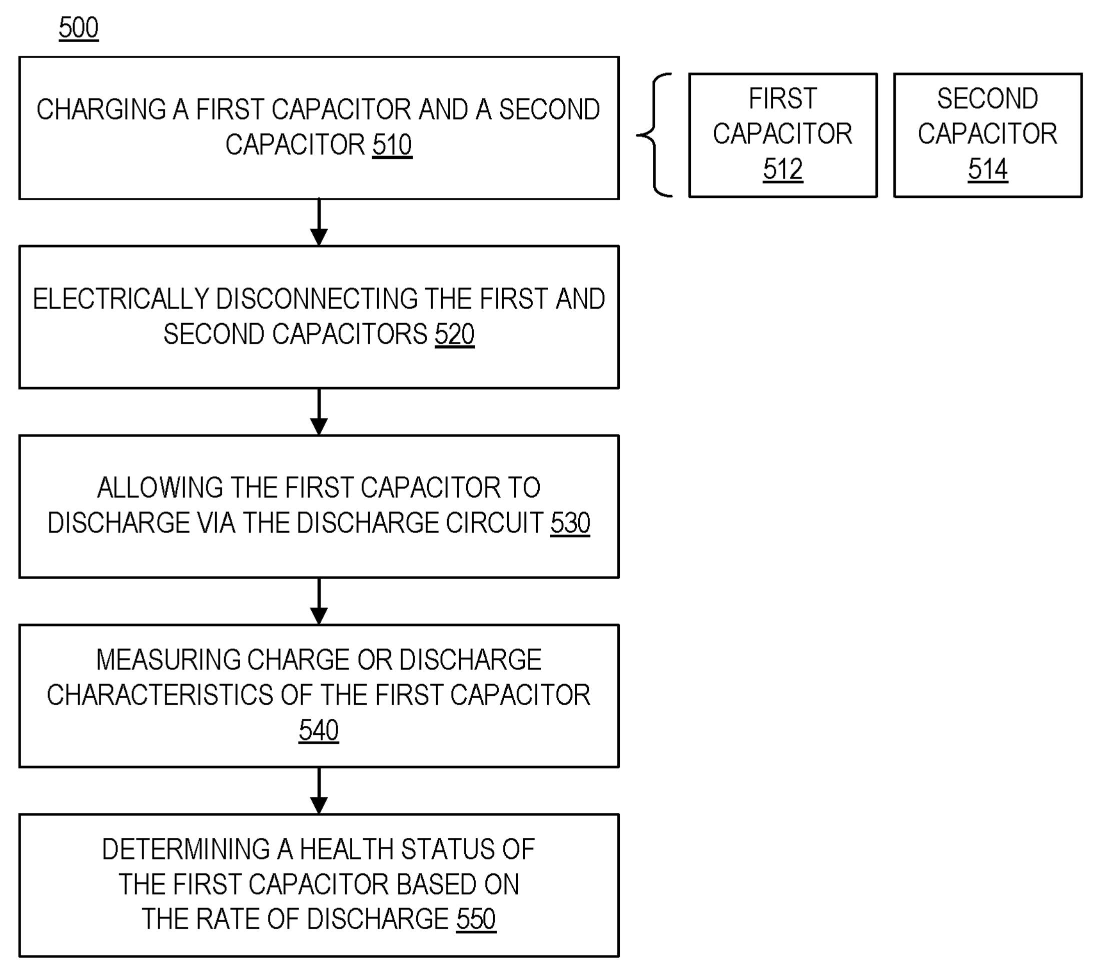
FIG. 5 illustrates a third example process for testing capacitors of an implantable stimulator in accordance with certain examples herein.

FIG. 5 illustrates a third example process 500 for testing one or more capacitors 204. The process 500 can begin with operation 510.

Operation 510 includes charging 510 a first capacitor 512 and a second capacitor 514. The capacitors 512, 514 can be charged using one or more techniques described elsewhere herein. Following operation 510, the flow of the process 500 can move to operation 520.

Operation 520 includes electrically disconnecting 520 the first capacitor 512 and the second capacitor 514. The disconnecting can include disconnecting the capacitors 512, 514 from all nodes except for tissue and a discharge circuit 114. This operation 520 can be performed after charging the first capacitor 512 and the second capacitor 514. For instance, switches 206 associated with the capacitors 512, 514 can be actuated to disconnect the capacitors 512 514 from one or more components (e.g., the stimulation source 112). Following operation 520, the flow of the process 500 can move to operation 530.

Operation 530 includes allowing the first capacitor 512 to discharge via the discharge circuit 114. This can include allowing the first capacitor 512 to discharge partially or entirely.

The process 500 can further include operation 540, which includes measuring charge or discharge characteristics of the first capacitor 512. This measuring can be performed before, during, or after operation 510, operation 520, and operation 530. For instance, during the charging of the first capacitor 512 and the second capacitor 514 in operation 510, the charging characteristics of the first capacitor 512 (as well as the second capacitor 514) can be measured. Likewise, while allowing the first capacitor 512 to discharge in operation 530, the discharge characteristics of the first capacitor 512 (as well as the second capacitor) can be measured. Following operation 540, the flow of the process 500 can move to operation 550.

Figure 6:
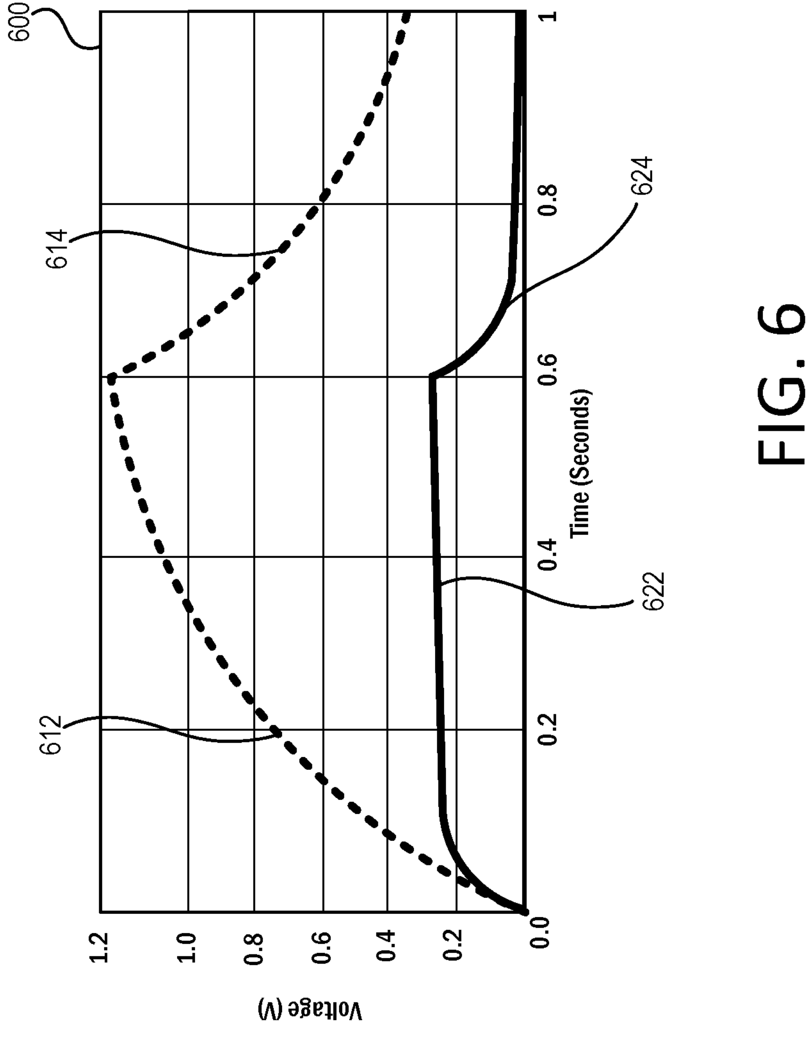
FIG. 6 illustrates a chart showing curves for a faulty capacitor and a healthy capacitor.

The charge or discharge characteristics can include, for example, a charging rate, a charging time, a charge curve, a discharge rate, a discharge time, or a discharge curve. An example charge curve and discharge curve for a healthy capacitor and a faulty capacitor are shown in FIG. 6.

Operation 550 includes determining a health status of the first capacitor 512 based on the charge or discharge characteristics. As described elsewhere herein, the characteristics can be compared against expected or known healthy characteristics. If the characteristics of the first capacitor 512 are sufficiently different from characteristics that a healthy capacitor 502 would have, then the first capacitor 512 can be determined to be faulty.

Responsive to the first capacitor 512 being determined to be healthy or unhealthy, one or more actions can be taken. For instance, where the first capacitor 512 is faulty, then stimulation associated with the first capacitor 512 can be disabled and the recipient or a clinician can be alerted.

Example Charge and Discharge Curves

FIG. 6 illustrates a chart 600 showing curves for a faulty capacitor and a healthy capacitor. In particular, the curves include a healthy capacitor charge curve 612, a healthy capacitor discharge curve 614, a faulty capacitor charge curve 622, and a faulty capacitor discharge curve 642.

In the illustrated example, the healthy capacitor charge curve 612 shows that an example healthy capacitor has a maximum voltage of approximately 1.2 volts and charges to approximately that maximum voltage in 0.6 seconds of monophasic stimulation. The faulty capacitor charge curve 622 reaches only approximately 0.25 volts during this time. These curves 612, 622 illustrate some ways in which the charging characteristics of faulty and healthy capacitors vary. As illustrated, one way to determine capacitor health is do determine how long a capacitor takes to reach a healthy maximum charge. As illustrated, a faulty capacitor would take significantly longer to reach the healthy maximum charge than a healthy capacitor. Thus if a capacitor takes longer than a threshold amount of time to reach a predetermined charge (e.g., the maximum charge), then the capacitor can be determined to be faulty. In another example, the amount of time that the capacitor takes to reach an equilibrium (e.g., the rate of change in the voltage decreases below a threshold). As illustrated, faulty capacitors may reach an approximate voltage equilibrium much quicker than a healthy capacitor. In the illustrated example, the rate of charge in the faulty capacitor charge curve 622 drops significantly at approximately 0.1 seconds, whereas the rate of charge for the healthy capacitor charge curve 612 reaches drops at approximately 0.6 seconds. In another example, the voltage of a capacitor can be checked at one or more time periods and if the voltage of the capacitor is differs from a healthy value by more than a threshold, then the capacitor can be determined to be faulty. For instance, at the time 0.2 seconds after charging begins, a healthy capacitor is expected to have a voltage of approximately 0.75 volts. If a capacitor's voltage after 0.2 seconds of charging differs from that by more than a threshold amount, then the capacitor can be determined to be faulty. In another example, the charge curves themselves can be compared. For example, approximate slopes of the curves can be determined and compared. For instance, if an approximate slope of a capacitor differs from a slope expected of a healthy capacitor by more than a threshold amount, then the capacitor can be determined to be faulty. In another example, an attempt can be made to fit a curve to the charge curve of a capacitor. If the fit differs by more than a threshold amount, then the capacitor can be determined to be faulty.

Similar analysis can be applied to discharge curves. For instance, in the illustrated example, the healthy capacitor discharge curve 614 shows that an example healthy capacitor discharges from approximately 1.2 volts to approximately 0.35 volts in approximately 0.4 seconds. And the faulty capacitor discharge curve 624 discharges from approximately 0.25 volts to approximately 0 volts in that same time period. As illustrated, the faulty capacitor discharges significantly quicker than a healthy capacitor. Thus if a capacitor takes less than a threshold amount of time to reach a predetermined charge (e.g., approximately 0 volts), then the capacitor can be determined to be faulty. In another example, the voltage of a capacitor can be checked at one or more time periods and if the voltage of the capacitor is differs from a healthy value by more than a threshold, then the capacitor can be determined to be faulty. For instance, at the time 0.2 seconds after discharge begins, a healthy capacitor is expected to have a voltage of approximately 0.6 volts. If a capacitor's voltage after 0.2 seconds of discharge differs from that by more than a threshold amount, then the capacitor can be determined to be faulty. In another example, the charge curves themselves can be compared. For example, approximate slopes of the curves can be determined and compared. For instance, if an approximate slope of a capacitor differs from a slope expected of a healthy capacitor by more than a threshold amount, then the capacitor can be determined to be faulty. In another example, an attempt can be made to fit a curve to the charge curve of a capacitor. If the fit differs by more than a threshold amount, then the capacitor can be determined to be faulty.

In addition, faulty capacitors can be identified by analyzing performance of a same capacitor over time. For instance, values produced from testing a capacitor can be stored and compared against at a later time to monitor potential degradation of capacitor performance over time.

While the above examples describe a binary determination of whether a capacitor is healthy or faulty, a health score can be applied to a capacitor. For instance, values from between 0 (completely faulty) and 1 (completely healthy) can be assigned to the capacitor based on the extent to which the capacitor matches a healthy capacitor. Such a determination can facilitate identification of capacitors that are beginning to fail that have not yet completely failed.

Example Devices

As previously described, the technology disclosed herein can applied in any of a variety of circumstances and with a variety of different devices. Example devices that can benefit from technology disclosed herein are described in more detail in FIGS. 7-9, below. For example, the implantable stimulator 100 can be part of a stimulation system 700, such as is shown in FIG. 7. In an example, the implantable stimulator 100 can be part of an auditory prosthesis, such as a cochlear implant as described in FIG. 8. As another example, implantable stimulator 100 can be a retinal prosthesis, such as is described in FIG. 9. The technology can be applied to other medical devices, such as neurostimulators, cardiac pacemakers, cardiac defibrillators, sleep apnea management stimulators, seizure therapy stimulators, tinnitus management stimulators, and vestibular stimulation devices, as well as other medical devices that deliver stimulation to tissue. These different sensory prostheses 110 can benefit from use with the systems and processes described above.

Example Implantable Stimulation System

FIG. 7 is a functional block diagram of an implantable stimulator system 700 that can benefit from techniques described herein. The implantable stimulator system 700 includes a stimulator device 701 and an external processor device 740. In examples, the stimulator device 701 is an implantable stimulator configured to be implanted beneath a recipient's tissue 749 (e.g., skin). In examples, the stimulator device 701 includes a biocompatible housing. The external processor device 740 is a device configured to couple with (e.g., wirelessly) the stimulator device 701 to provide additional functionality. In examples, the stimulator device system 700 includes a charger device 790 in addition to or instead of the external processor device 740.

In the illustrated example, the stimulator device 701 includes an electronics module 110, a stimulator assembly 130, a transceiver unit 140 and a battery 150 as described in FIG. 1 and further includes a coil 709 and an auxiliary connector unit 720. The stimulator device 701 further includes a hermetically sealed, biocompatible housing enclosing one or more of the components.

The auxiliary connector unit 720 is a component of the stimulator device 701 for connecting the stimulator device 701 to the auxiliary device 750 via the implantable cable 760. In some examples the auxiliary connector unit 720 includes a port to which the implantable cable 760 is coupled, thereby electrically coupling the stimulator device 701 and the auxiliary device 750. In some examples, the auxiliary connector unit 720 includes one or more switches or other components for managing the flow of data or power across the implantable cable 760 to and from the auxiliary device 750.

The external processor device 740 can be a component of the system 700 configured to perform processing and control stimulation provided by the stimulator unit. In other examples, the external processor 740 can be a fitting device for fitting the implantable stimulator 710. In the illustrated example, the external processor device 740 includes one or more sensors 742, a processor 744, a transceiver unit 746, and a power source 748. The one or more sensors 742 are each units configured to produce data based on sensed activities. In an example where the stimulation system 700 is an auditory prosthesis system, the one or more sensors 742 can include sound input sensors, such as a microphone, an electrical input for an FM hearing system, and/or another component for receiving sound input. Where the stimulation system 700 is a visual prosthesis system, the one or more sensors 742 can include one or more cameras or other visual sensors. Where the stimulation system 700 is a cardiac stimulator, the one or more sensors 742 can include cardiac monitors. The processor 744 can be configured to control stimulation provided by the implantable stimulator. The stimulation can be controlled based on data from the sensor 742, a stimulation schedule, or other data. Where the stimulation system 700 is an auditory prosthesis, the processor 744 can be configured to convert sound signals received from sound input unit 742 into external device data signals 753. The transceiver 746 is configured to send an external device power signal 751, an external device data signal 753, combinations thereof (e.g., by interleaving the signals), or other signals. The transceiver 746 can also be configured to receive power or data. Stimulation signals can be generated by the processor 744 and transmitted, using the transceiver 746, to the stimulator device 701 for use in providing stimulation.

The auxiliary device 750 is an implantable component remote from the stimulator device 701 and configured to provide an auxiliary signal to the stimulator device 701. In this manner, the auxiliary device 750 supports the stimulator device 701. The auxiliary device 750 includes a stimulator device connector unit 755, an auxiliary component 752 for generating the auxiliary signal, and an auxiliary device battery 754 for powering one or more components of the auxiliary device 750, such as the auxiliary component 752. The implantable cable 760 is a component comprising one or more wires for providing a wired electrical connection between the stimulator device 701 and the auxiliary device 750.

The stimulator device connector unit 755 is a component of the auxiliary device 750 enabling the connection to the auxiliary device 750 to the stimulator device 701 via the implantable cable 760. In some examples the stimulator device connector unit 755 includes a port to which the implantable cable 760 is coupled, thereby electrically coupling the stimulator device 701 and the auxiliary device 750.

The auxiliary component 752 is a component of the auxiliary device 750 that provides functionality to the system 700. For instance, the auxiliary component 752 generates an auxiliary signal provided from the auxiliary device 750 to the stimulator device 701. Where the stimulation system 700 is an auditory stimulation system, the auxiliary component 752 can be or include one or more components of the group of: a microphone, a transcutaneous wireless audio link, and a subcutaneous wireless audio link, among other components. And the audio produced by the auxiliary components 752 can be provided to the stimulator device 701 (e.g., the electronics module thereof) as a signal for use in generating the stimulation signals 715. Where the stimulation system 700 is a cardiac stimulation system, the auxiliary component 752 can be a cardiac sensor that produces data based on which the implantable stimulator 701 can produce stimulation. In addition to or instead of the foregoing components, the auxiliary component 752 can be or include a transcutaneous wireless stimulation data link, a subcutaneous wireless stimulation data link, or a telecoil, among other components. In another example (e.g., where the stimulation system 700 includes a vestibular stimulation system), the auxiliary component 752 includes an accelerometer that generates accelerometer signals that are provided to the stimulator device 701 as the auxiliary signal for use in generating the stimulation signals 715.

In an example, the auxiliary component 752 is a command receiver (e.g., for receiving commands sent of an RF protocol) to receive commands transmitted from another device (e.g., a non-implanted remote control device). In examples, the auxiliary component 752 is a sensor (e.g., magnetic field sensor) for detecting whether the system 700 is being subject to MRI (Magnetic Resonance Imaging) and for sending an auxiliary signal to deactivate or activate one or more components of the system 700 (e.g., the implantable stimulator 701) based thereon. In an example, the auxiliary component 752 controls the system 700 such that the implantable stimulator 701 is inoperable absent cooperation with the auxiliary component 752. In such examples, the auxiliary component 752 can act like a main control or key that permits operation of the implantable stimulator. In an example, the system 700 is configured such that the auxiliary battery 754 does not empty before the stimulator device battery 712.

The auxiliary device battery 754 is a rechargeable battery. In an example, the auxiliary device battery 754 is a lithium ion battery. The auxiliary device battery 754 can be charged by the implantable stimulator 701.

The charger device 790 is an optional device configured to charge the stimulator device 701 by providing a power signal 751. The charger device 790 includes a power source 748 and a transceiver unit 746. Compared to the external processor device 740, the charger device 790 lacks a sound processor 744 and a sound input unit 742. As such, in many examples the charger device 790 provides only a power signal 751 and not a data signal 753. In some examples, the external processor device 740 can be set to a charger mode such that the external processor device 740 acts as a charger device (e.g., by disabling functionality to provide only a power signal 751 and not a data signal 753).

As should be appreciated, while particular components are described in conjunction with FIG. 7, technology disclosed herein can be applied in any of a variety of circumstances. The above discussion is not meant to suggest that the disclosed techniques are only suitable for implementation within systems akin to that illustrated in and described with respect to FIG. 7. In general, additional configurations can be used to practice the methods and systems herein and/or some aspects described can be excluded without departing from the methods and systems disclosed herein.

Example Sensory Prostheses—Cochlear Implant System

Figure 8:
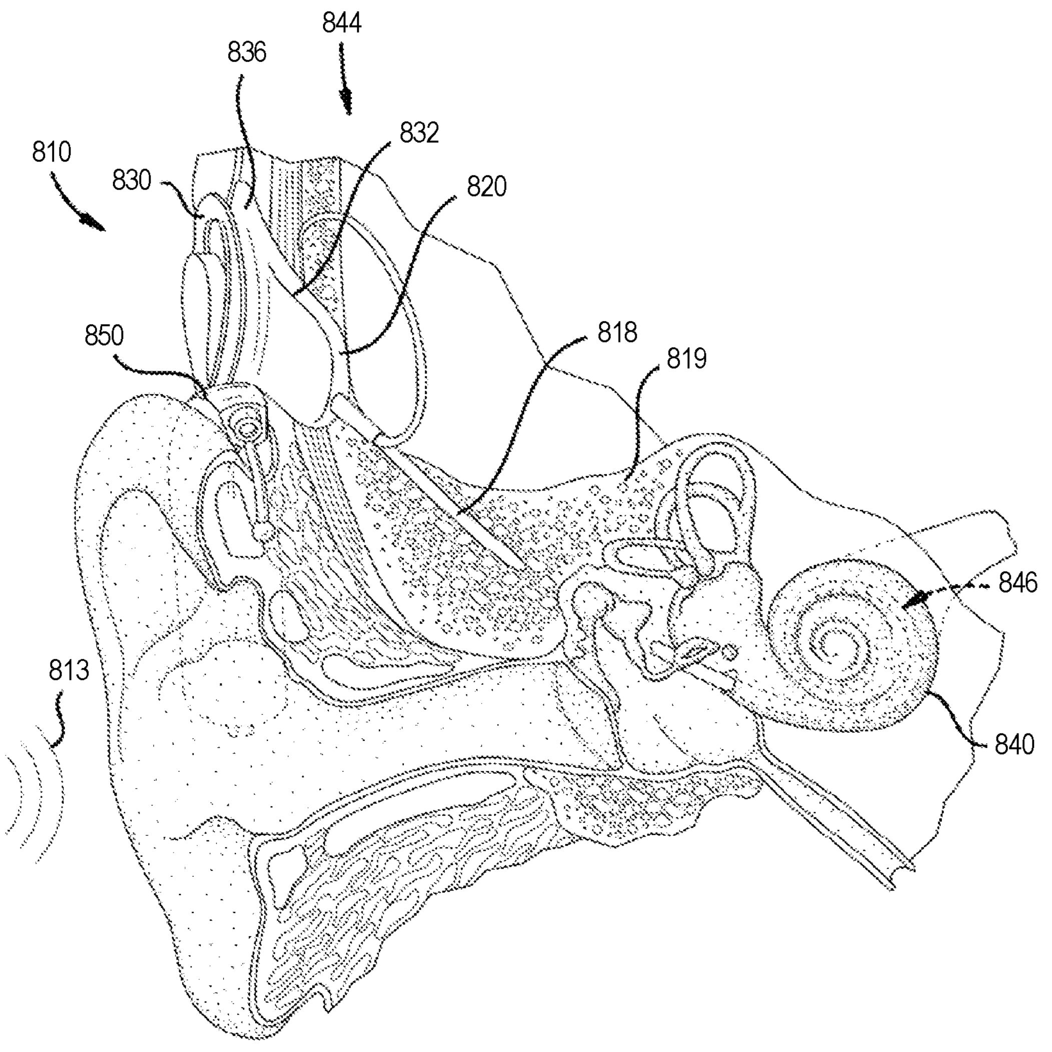
FIG. 8 illustrates an example cochlear implant system that can benefit from use of the technologies disclosed herein.

FIG. 8 illustrates an example cochlear implant system 810 that can benefit from use of the technologies disclosed herein. The cochlear implant system 810 includes an implantable component 844 typically having an internal receiver/transceiver unit 832, a stimulator unit 820, and an elongate lead 818. The internal receiver/transceiver unit 832 permits the cochlear implant system 810 to receive signals from and/or transmit signals to an external device 850. The external device 850 can be a button sound processor worn on the head that includes a receiver/transceiver coil 830 and sound processing components. Alternatively, the external device 850 can be just a transmitter/transceiver coil in communication with a behind-the-ear device that includes the sound processing components and microphone.

The implantable component 844 includes an internal coil 836, and preferably, a magnet (not shown) fixed relative to the internal coil 836. The magnet can be embedded in a pliable silicone or other biocompatible encapsulant, along with the internal coil 836. Signals sent generally correspond to external sound 813. The internal receiver/transceiver unit 832 and the stimulator unit 820 are hermetically sealed within a biocompatible housing, sometimes collectively referred to as a stimulator/receiver unit. Included magnets (not shown) can facilitate the operational alignment of an external coil 830 and the internal coil 836, enabling the internal coil 836 to receive power and stimulation data from the external coil 830. The external coil 830 is contained within an external portion. The elongate lead 818 has a proximal end connected to the stimulator unit 820, and a distal end 846 implanted in a cochlea 840 of the recipient. The elongate lead 818 extends from stimulator unit 820 to the cochlea 840 through a mastoid bone 819 of the recipient. The elongate lead 818 is used to provide electrical stimulation to the cochlea 840 based on the stimulation data. The stimulation data can be created based on the external sound 813 using the sound processing components and based on the sensory prosthesis settings 146.

In certain examples, the external coil 830 transmits electrical signals (e.g., power and stimulation data) to the internal coil 836 via a radio frequency (RF) link. The internal coil 836 is typically a wire antenna coil having multiple turns of electrically insulated single-strand or multi-strand platinum or gold wire. The electrical insulation of the internal coil 836 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Example Medical Device—Retinal Prosthesis

Figure 9:
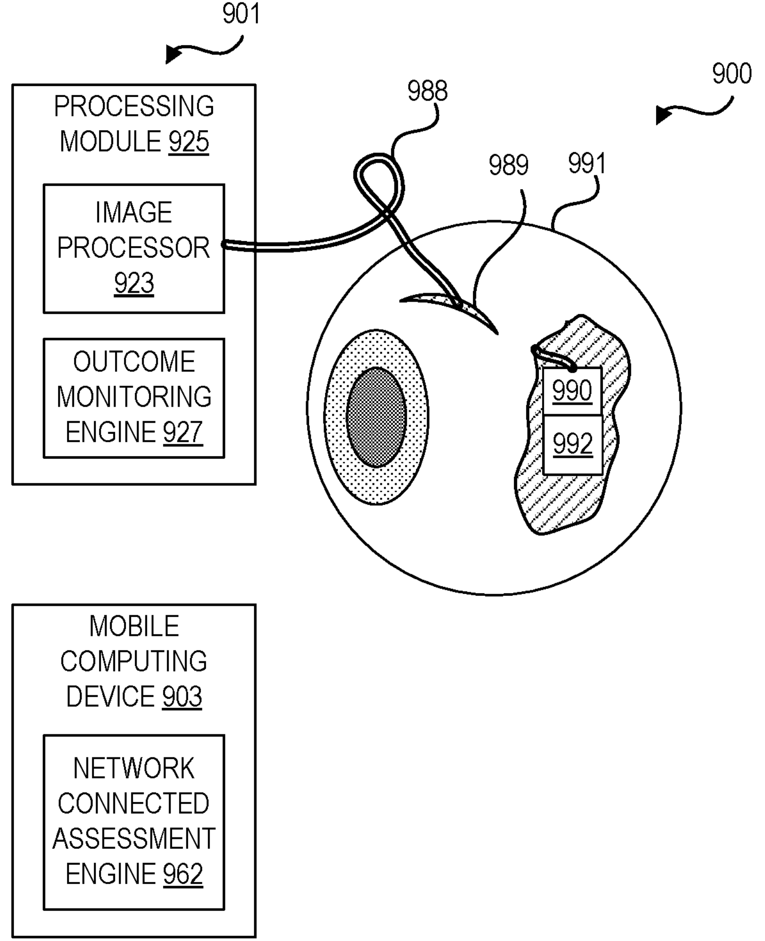
FIG. 9 illustrates a retinal prosthesis system that comprises a retinal prosthesis and a mobile computing device that can benefit from use of the technologies disclosed herein.

FIG. 9 illustrates a retinal prosthesis system 901 that comprises a retinal prosthesis 900 and a mobile computing device 903. The retinal prosthesis 900 comprises a processing module 925 and a retinal prosthesis sensor-stimulator 990 is positioned proximate the retina 991 of a recipient. In an example, sensory inputs (e.g., photons entering the eye) are absorbed by a microelectronic array of the sensor-stimulator 990 that is hybridized to a glass piece 992 including, for example, an embedded array of microwires. The glass can have a curved surface that conforms to the inner radius of the retina. The sensor-stimulator 990 can include a microelectronic imaging device that can be made of thin silicon containing integrated circuitry that convert the incident photons to an electronic charge.

The processing module 925 includes an image processor 923 that is in signal communication with the sensor-stimulator 990 via, for example, a lead 988 which extends through surgical incision 989 formed in the eye wall. In other examples, processing module 925 can be in wireless communication with the sensor-stimulator 990. The image processor 923 processes the input into the sensor-stimulator 990, and provides control signals back to the sensor-stimulator 990 so the device can provide an output to the optic nerve. That said, in an alternate example, the processing is executed by a component proximate to, or integrated with, the sensor-stimulator 990. The electric charge resulting from the conversion of the incident photons is converted to a proportional amount of electronic current which is input to a nearby retinal cell layer. The cells fire and a signal is sent to the optic nerve, thus inducing a sight perception.

The processing module 925 may be implanted in the recipient or may be part of an external device, such as a Behind-The-Ear (BTEA) unit, a pair of eyeglasses, etc. The retinal prosthesis 900 can also include an external light/image capture device (e.g., located in/on a BTE device or a pair of glasses, etc.), while, as noted above, in some examples, the sensor-stimulator 990 captures light/images, which sensor-stimulator is implanted in the recipient.

Similar to the above examples, the retinal prosthesis system 901 may be used in spatial regions that have at least one controllable network connected device associated therewith (e.g., located therein). As such, the processing module 925 includes a performance monitoring engine 927 that is configured to obtain data relating to a "sensory outcome" or "sensory performance" of the recipient of the retinal prosthesis 900 in the spatial region. As used herein, a "sensory outcome" or "sensory performance" of the recipient of a sensory prosthesis, such as retinal prosthesis 900, is an estimate or measure of how effectively stimulation signals delivered to the recipient represent sensor input captured from the ambient environment.

Data representing the performance of the retinal prosthesis 900 in the spatial region is provided to the mobile computing device 903 and analyzed by a network connected device assessment engine 962 in view of the operational capabilities of the at least one controllable network connected device associated with the spatial region. For example, the network connected device assessment engine 962 may determine one or more effects of the controllable network connected device on the sensory outcome of the recipient within the spatial region. The network connected device assessment engine 962 is configured to determine one or more operational changes to the at least one controllable network connected device that are estimated to improve the sensory outcome of the recipient within the spatial region and, accordingly, initiate the one or more operational changes to the at least one controllable network connected device.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. For examples, while certain technologies described herein were primarily described in the context of auditory prostheses (e.g., cochlear implants), technologies disclosed herein are applicable to medical devices generally (e.g., medical devices providing pain management functionality or therapeutic electrical stimulation, such as deep brain stimulation). In general, additional configurations can be used to practice the processes and systems herein and/or some aspects described can be excluded without departing from the processes and systems disclosed herein. Further, the techniques described herein can be applicable to determining a recipient's response to other stimuli, such as visual stimuli, tactile stimuli, olfactory stimuli, taste stimuli, or another stimuli. Likewise, the devices used herein need not be limited to auditory prostheses and can be other medical devices configured to support a human sense, such as bionic eyes.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A method comprising:

selecting one or more electrodes of a plurality of electrodes of an implantable stimulator as an active electrode set for testing one or more active electrode capacitors associated with the active electrode set;

selecting one or more electrodes of the plurality of electrodes as a return electrode set for testing the one or more active electrode capacitors associated with the active electrode set;

charging the one or more active electrode capacitors associated with the active electrode set;

charging one or more return electrode capacitors associated with the return electrode set;

disconnecting the return electrode set, the active electrode set, the one or more active electrode capacitors, and the one or more return electrode capacitors from a stimulation source;

after disconnecting, measuring one or more characteristics of the one or more active electrode capacitors during discharge of the one or more active electrode capacitors; and determining a health of one or more of the one or more active electrode capacitors based on the one or more characteristics.

2. The method of claim 1, wherein the one or more characteristics include an amount of time taken to discharge the one or more active electrode capacitors or a discharge curve of the one or more active electrode capacitors, and wherein the method further comprises:

determining the health of one or more of the one or more active electrode capacitors at least in part on the amount of time taken to discharge the one or more active electrode capacitors or a discharge curve of the one or more active electrode capacitors.

3. The method of claim 2, wherein determining the health of the one or more active electrode capacitors based on an amount of time includes:

determining that one or more of the one or more active electrode capacitors is faulty responsive to the one or more characteristics failing to satisfy a predetermined threshold.

4. The method of claim 3, wherein the predetermined threshold is based on a calculated discharge time.

5. The method of claim 1, further comprising:

identifying one or more faulty capacitors based on the determined health; and disabling one or more electrodes associated with the one or more faulty capacitors.

6. The method of claim 1, wherein the one or more active electrode capacitors discharge over a discharge circuit comprising a star circuit of resistors.

7. The method of any one of claim 1, wherein the disconnecting includes:

disconnecting via one or more switches.

8. An implantable stimulator comprising:

a stimulation source;

a plurality of electrode subcircuits, each respective electrode subcircuit having:

a capacitor, an electrode connected in series to the capacitor and being configured to deliver stimulation to tissue using the stimulation source, and a switch connected to the capacitor and configured to selectively couple the capacitor with the stimulation source;

a discharge circuit connected to each of the plurality of electrode subcircuits; and one or more processors configured to test, during a power-on process of the implantable stimulator or during a fitting of the implantable stimulator, a health status of a respective capacitor of a respective electrode subcircuit of the plurality of electrode subcircuits via a test, wherein the test includes:

charging the respective capacitor;

designating an electrode subcircuit of the plurality of electrode subcircuits as a return electrode subcircuit;

charging a return capacitor associated with the return electrode subcircuit;

disconnecting the respective capacitor and the return capacitor from the stimulation source;

determining discharge characteristics of the respective capacitor while discharging via the discharge circuit; and determining the health status of the respective capacitor based on the discharge characteristics.

9. The implantable stimulator of claim 8, wherein the discharge characteristics include an amount of time the respective capacitor takes to discharge via the discharge circuit.

10. The implantable stimulator of claim 8, wherein the discharge circuit comprises a node connected to each of the plurality of electrode subcircuits via a respective discharge subcircuit comprising a resistor.

11. The implantable stimulator of claim 8, wherein the discharge circuit is electrically connected to each respective electrode subcircuit of the plurality of electrode subcircuits between a capacitor and a switch of the respective electrode subcircuit.

12. The implantable stimulator of claim 8, wherein the stimulation source is configured to provide biphasic stimulation.

13. The implantable stimulator of claim 8, wherein the implantable stimulator is at least one of: a cochlear implant, a neurostimulator, a tinnitus management stimulator, or a visual prosthesis.

14. A method comprising;

identifying, using an assessment plan that identifies a plurality of tests to perform and, for each test, a plurality of electrodes to select for performing the test, a first electrode for testing a first capacitor associated with the first electrode;

identifying, using the assessment plan, a second electrode for testing the first capacitor;

charging the first capacitor and a second capacitor associated with the second electrode;

after charging the first capacitor and the second capacitor, electrically disconnecting the first capacitor and the second capacitor from all nodes except for tissue and a discharge circuit;

allowing the first capacitor to discharge via the discharge circuit;

measuring charge or discharge characteristics of the first capacitor; and determining a health status of the first capacitor based on the charge or discharge characteristics.

15. The method of claim 14, wherein the charge or discharge characteristics include a charging rate or a charge curve.

16. The method of claim 14, wherein the charge or discharge characteristics include a discharge rate or a discharge curve.

17. The method of claim 14, wherein charging the first capacitor and the second capacitor include charging the first capacitor and the second capacitor using monophasic stimulation.

18. The method of claim 14, further comprising using a reference electrode to measure a rate of discharge of the first capacitor.

19. The method of claim 14, wherein the first capacitor is a capacitor of a set of one or more active electrode capacitors associated with one or more active electrodes, and wherein the second capacitor is a capacitor of a set of one or more return electrode capacitors associated with one or more return electrodes.

20. The implantable stimulator of claim 8, wherein the discharge circuit comprising a star circuit of resistors.

* * * * *